US00RE43391E

(19) United States
(12) Reissued Patent
Costin et al.

(10) Patent Number: US RE43,391 E
(45) Date of Reissued Patent: *May 15, 2012

(54) DATABASE PROGRAM WITH AUTOMATIC CREATION OF USER FEATURES

(75) Inventors: Darryl Costin, Westlake, OH (US); Clarence Martin, Gahanna, OH (US)

(73) Assignee: Straform Data Mgmt Limited Liability Company, Wilmington, DE (US)

( * ) Notice: This patent is subject to a terminal disclaimer.

(21) Appl. No.: 11/965,372

(22) Filed: Dec. 27, 2007

Related U.S. Patent Documents

Reissue of:
(64) Patent No.: 7,031,960
Issued: Apr. 18, 2006
Appl. No.: 09/703,482
Filed: Oct. 31, 2000

U.S. Applications:
(63) Continuation of application No. 09/082,419, filed on May 20, 1998, now Pat. No. 6,178,413.

(51) Int. Cl.
*G06F 7/00* (2006.01)
*G06F 17/30* (2006.01)

(52) U.S. Cl. ..... 707/760; 707/769

(58) Field of Classification Search ..... 707/3–5, 707/103, 736, 758, 759, 760, 769, 999.003–999.004
See application file for complete search history.

(56) References Cited

U.S. PATENT DOCUMENTS

| | | | | |
|---|---|---|---|---|
| 4,939,689 | A * | 7/1990 | Davis et al. | 707/102 |
| 5,428,735 | A * | 6/1995 | Kahl et al. | 715/839 |
| 5,649,182 | A * | 7/1997 | Reitz | 707/7 |
| 5,787,418 | A * | 7/1998 | Hibbetts et al. | 707/4 |
| 5,924,089 | A * | 7/1999 | Mocek et al. | 707/4 |
| 6,067,568 | A * | 5/2000 | Li et al. | 709/223 |
| 6,078,314 | A * | 6/2000 | Ahn | 345/169 |
| 6,154,745 | A * | 11/2000 | Kari et al. | 705/1.1 |
| 6,178,413 | B1 * | 1/2001 | Costin | 1/1 |
| 6,182,069 | B1 * | 1/2001 | Niblack et al. | 707/6 |

OTHER PUBLICATIONS

"Database Access with Visual Basic", Jeffrey Mcmanus ,Publisher: Macmillan Computer Publishing.*

* cited by examiner

*Primary Examiner* — Hung T Vy
(74) *Attorney, Agent, or Firm* — Brundidge & Stanger, P.C.

(57) ABSTRACT

Integrated document management system automatically creates pull down lists and pop up buttons based on the project specifications.

44 Claims, 8 Drawing Sheets

A. LIST POTENTIAL WITNESSES

| PROSECUTION | DEFENSE |
|---|---|
| JOHN DOE | JIM JONES |
| AL JACKSON | DICK KINDER |
| GLORIA TIMS | DEE CLARKS |
| SUE ALKS | JOE MANNS |
| FRED YORK | JENNY BICS |

B. LIST PEOPLE WHO SEND, RECEIVE OR ARE COPIED ON MEMOS AND CORRESPONDENCE

| | | |
|---|---|---|
| AL KILKA | FRED YORK | JENNY BICS |
| JOE CURL | JIM JONES | TOM ULNER |
| SALLY DOPER | JUDY KALMER | BING STUBY |
| JUDY FIELDS | DICK KINDER | CAROL SLIP |
| JOHN DOE | DEE CLARKS | KIM CARASONS |
| AL JACKSON | JIM GRANDER | JOHN JENSEN |
| TIM YANS | DEB DUCKER | HEATHER BATIA |
| AL YU | | |

C. LIST CATAGORIES

BANKS

CONSULTING CONTRACTS

GOVERNMENT CONTRACTS

TAXES

FOREIGN SUBSIDIARIES

FIG. 1A

D. LIST SOURCES OF DOCUMENTS

| | |
|---|---|
| DEPOSITION | BANKS |
| NEWS | COMPANY A |
| MOTIONS | COMPANY B |
| CASE LAW | COMPANY C |

E. LIST LEGAL ARGUMENTS ANTICIPATED

LACK OF INTENT
CHARACTER
FAIRNESS
DISCLOSURE
ARMS LENGTH
THIRD PARTY ENDORSMENT

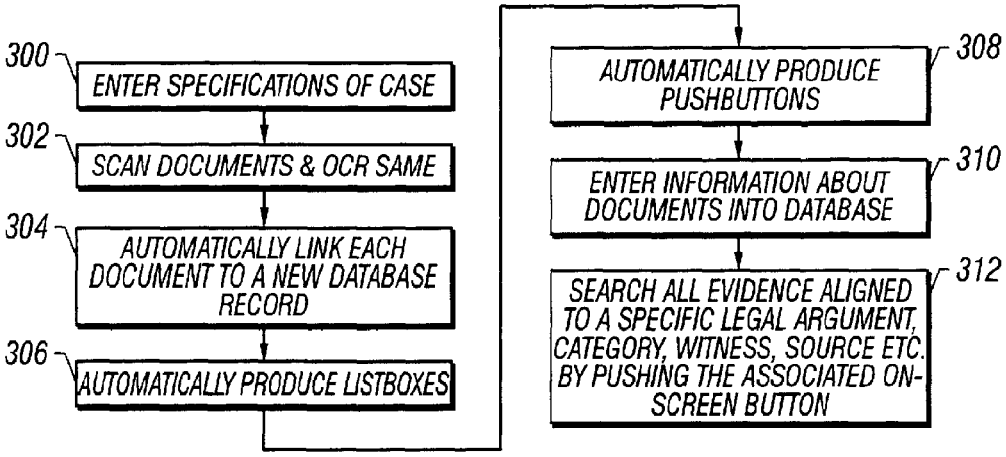

FIG. 3

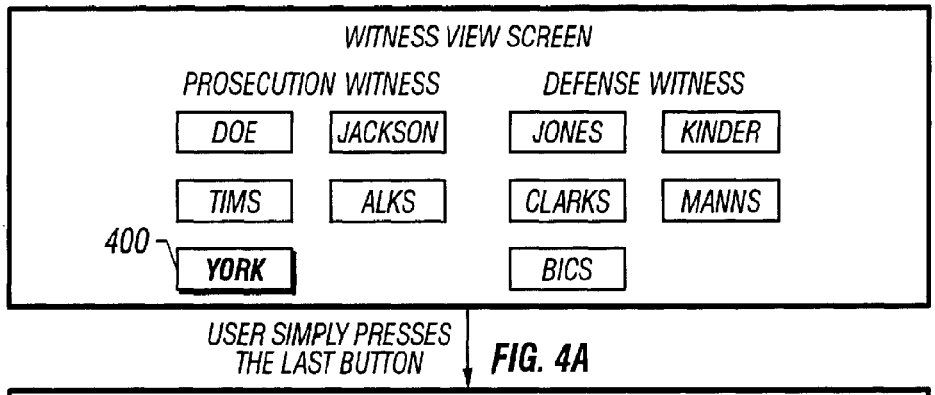

USER SIMPLY PRESSES THE LAST BUTTON

FIG. 4A

SORTED REPORT FOR FRED YORK

350

| BATES # | DATE | AUTHOR | SUMMARY | VIEW DOCUMENT |
|---|---|---|---|---|
| CQ1091138 | 2-11-94 | TED KRAMER | MEMO RE BANK FINANCING | ☐ |
| CQ2101773 | 4-08-95 | FRED YORK | FEDERAL TAX RETURN | ☐ |
| LL09645 | 5-15-95 | FRED YORK | MEMO RE BANKING ALTERNATIVES | ☐ |
| Z4114199 | 6-20-96 | AL JACKSON | HANDWRITTEN NOTES RE FUNDING | ☐ |
| Z5632114 | 6-21-96 | FRED YORK | NOTES ON EXECUTIVE MEETING | ☐ |
| CQ0199432 | 7-15-97 | SUE ALKS | MINUTES OF FINANCING CONTRACT MEETING WITH BANK | ☐ |
| LL143269 | 8-12-97 | JENNY BICS | SALARY ANNUAL FOR YORK | ☐ |
| Z900046 | 8-18-98 | FRED YORK | CASH FLOW DIAGRAM | ☐ |

USER SIMPLY PRESSES THE LAST BUTTON

FIG. 4B

A

DATABASE PROGRAM WITH AUTOMATIC CREATION OF USER FEATURES

Matter enclosed in heavy brackets [ ] appears in the original patent but forms no part of this reissue specification; matter printed in italics indicates the additions made by reissue.

This is a continuation of [08/082,419 filed Jun. 28, 1993, now U.S. Pat. No. 5,494,677, which is a continuation of appl. Ser. No. 07/876,783, filed Apr. 30, 1992, now U.S. Pat. No. 5,326,568.] *Ser. No. 09/082,419, filed May 20, 1998, now U.S. Pat. No. 6,178,413.*

BACKGROUND

Organization of information is perhaps the most important function of computers. Many different organizations use computers to maintain a vast array of documents. This organization is most often done with a database, or document management and integrated database program.

The basic methodology in software applications that offer this form of document management is a structured database.

One drawback of the structured database, however, is the level of sophistication that is required of the system's users. Extensive training is generally required before users of the system can perform even the most basic functions.

The inventor of the present invention has recognized that the conventional database and document management software suffers from significant drawbacks because they are so hard to use. Inexperienced computer programmers have difficulty in learning to use the database software. Even those who eventually learn, do so only after investing many man hours of work in that learning process. This is economically very costly.

Even once that initial investment has been made, the system is so complicated that it is not feasible to change the database without significant rework. Customization of the existing process cannot be done easily. The user must typically write code or make a new arrangement to effect this new customization.

A generic database program such as Microsoft Access and Lotus Approach allow any desired task to be carried out if appropriately programmed into the system. The appropriate programming for such a system, as noted above, requires significant learning curves to program and master. This would not typically be used by the average lawyer, since they do not have the time or inclination to master the intricacies of such. This is so well recognized that software vendors go through great efforts to offer technical seminars and training sessions on how to use their database and document management software applications. The programs are provided with thick owner's manuals including tutorials which show the user how to use the product.

For example to set-up Microsoft's Access (which is the leading database program in the nation) for use in a specific area, one must go through the following rather complicated steps:

- Set up a table of the description and validation rules for a variety of fields
- Assign each field of the table a set of properties such as field name, data type, description, primary key, field size, format, decimal places, input mask, caption, default value, index parameter, validation parameters, etc

- Develop a data entry input screen layout
- Enter, edit and validate data
- Develop the mechanism for sorting, finding and filtering data in tables
- Define simple to complex queries to collect specific information
- Create and design different custom forms for the collection of data
- Design the screen layouts for the generation of reports.
- Develop macros to automate a series of procedural steps.
- Write programs in Visual basic to enable advanced features Several third-party textbooks on using Microsoft Access dedicate over 1000 pages to explaining how to accomplish the above ten steps! Having completed this series of complicated tasks which require a considerable degree of computer savvy, the user then has a custom database program for one specific need. The program cannot be easily transferred to another need. For example, a database set-up for collecting documents in a specific legal case may not be applicable for another case, since the scope of the case may change from civil fraud to criminal tax evasion, for example. The number and type of database fields will change, the type of searches and queries will change and the required reports will change. The corresponding legal arguments, categories of documents, sources of documents, etc. would change as the case changes. Of course, a specific database designed for one specific legal case will likely have no applications for medical, research or general corporate document management needs.

Access does allow for the creation of macro buttons such that the user can press a button and get specific information based upon a simple or complex query. However, the button must first be programmed and then it only applies to the one query specific for the one database in use. As above, this process requires multiple man-hours of work.

For example, a typical Access task might take 4 hours to learn. A lawyer who bills $300 per hour therefore gives up $1200 to learn that task. And, this is only one task. It can be seen that these tasks can be extraordinarily expensive to carry out. A busy professional simply cannot afford to learn these tasks.

Users of database information often employ sizable Management Information Services ("MIS") departments to operate and train in-house staff on the use of such typical document database applications.

A Case Management System describes a Key Entry Database software application which is optimized for use in the legal profession. The software is really a structured database that stores information about the specific documents that the user enters in the computer and allows for the browsing and reporting of information based on a number of different search options. For example, a database could be designed to record important information about a set of documents such as the author, recipient, subject, carbon copy, date, bates number, source, summary, legal argument, etc. The user would enter such information into the database. Then the user needs to learn to program the database to produce a variety of reports based on simple to complex queries. Part of that query can include appropriate sorting by date, author, subject, category, legal argument, source, etc.

Document management products are specialized database programs. These rely on some form of a document database often referred to as a Key Entry Database. The user interacts with a Key Entry Database using the standard Graphical User Interface "GUI". Components of a GUI include pull-down menus, scroll bars, dialog boxes, and moveable resizable windows.

GUI's have made many aspects of operation of the computer system more intuitive. However, GUIs were designed to facilitate interaction with a wide variety of application types such as spreadsheet, word processing, drawing and charting, scheduling and program development, as well as database management and to provide sophisticated features for "power users". Therefore, it is not surprising that many talented professionals are overwhelmed upon their initial introduction to Key Entry Databases and never become capable users. The inventor recognized that those individuals would be better served by a system that provided precisely those tools that met their needs in as simple a manner as possible.

A number of different software products exist on the market, including Abacus Law, Amicus Attorney, CasePro, LegalEdge, Pro Cura, ProLaw, Case Map, Trial Works, and Saga System. These systems are not easy to use. It is not easy to enter data, establish custom configurations unique to the needs of the user and most importantly fetch information and reports from simple to complex queries and searches.

SUMMARY

The present system defines a technique allowing automatic creation of appropriate information based on entered data. A result of this automatic creation as described herein is the formation of custom databases of information without programming or specialized learning. The databases are created automatically from initial specifications of the information.

The specifications are automatically organized using tools allowing unprecedented simple searching and reporting of the requested information—push buttons and a single column pop up list box. This allows the users to simply press appropriate buttons to secure the information they require from the database.

The system prompts the user to enter the specifications of their case or database on a start-up screen. These specifications are automatically parsed into set forms including push buttons and pop-up list boxes. The push buttons and pop-up list boxes are automatically created from the input information and the input documents.

Many of the operations done by this system could have been manually done, using complex programming operations, in any database program. However, no one, to the knowledge of the inventor, has ever carried out the specific operations as described herein and which has been found to have advantageous results.

For example, in the above-alluded manual process, the programmer could first create a complex query providing instructions to search for all documents which John Doe authored, received, was copied on or was mentioned in. After that complex process, the user may later be interested in all documents associated with Jane Doe. The complicated process of creating complex queries and associating these queries with macros would then need to be repeated.

This invention relates to a novel concept to automatically convert initial database-type specifications to simplified push-button controls. Each push button control is a control having a title. The title includes an associated selectable area on said screen that is initable with a single initiation to allow the easy retrieval of information in the database. One example is the push button command box in the Windows interface, in which the single initiation can be, for example, a click of a mouse. A similar action could be initiated by a push on a touch screen, for example.

The present invention describes a specialized system for management of data using an automatically-generated customized user interface. This customized user interface includes customized push buttons allowing a plurality of operations to be carried out. Menus or dialogs are preferably not used with these operations that are carried out using push buttons. The inventor found that this allows users with limited computer experience such as doctors, trial attorneys and many corporate employees to use the program very easily and without extensive training.

In addition to the automatically created push button interface noted above, the present invention also includes automatic creation of the contents of list boxes to facilitate data entry.

BRIEF DESCRIPTION OF THE DRAWINGS

These and other aspects of the invention and embodiments will now be described in detail with respect to the accompanying drawings, in which:

FIGS. 1A, 1B and 2 show user interface screens for entering initial specifications of a project;

FIG. 3 shows a flowchart of operation of entering those specifications of the case;

FIGS. 4A-4C shows screens which are automatically produced by the specifications that are entered;

DESCRIPTION OF THE PREFERRED EMBODIMENTS

A preferred embodiment as described herein explains how this system could be used as a litigation support system. In this system, any person, including a trial attorney who is not trained in using this system, can powerfully interact and obtain information from the system.

The system automatically produces proper "push buttons" as described herein. A push button as used herein, means a labeled portion of a computer screen which can be actuated to carry out some action associated with the label. In Windows GUI, the push button is often actually shaped like a button, looks like a button, and has a title in the area to be selected. The user can simply select the area of the screen corresponding to the button to obtain additional information associated with the title.

The system can also be adapted for use in any other case by simply entering new specifications. This automatically creates a new set of buttons.

The way in which the documents and information are entered into the system is illustrated with reference to the user interface screens shown in FIGS. 1A, 1B and 2, and the overall system flowchart shown in FIG. 3.

FIG. 1A illustrates the first part of the start-up screen which requests the user to enter the specifications of the project, here a litigation case. This embodiment of a litigation support document database requires only five classifications of information to have specifications associated therewith. It should be understood that further information can also be added, and processed according to the teachings of this specification.

Field A is a list of potential witnesses for the case. This list can be expanded or contracted as the case progresses. Each change of the list automatically produces additional corresponding information.

Field B is a list of those people on the documents that will be entered into the database. As documents are added into the database, each author, recipient, carbon copied recipient ("cc") is entered into the field B.

Field C is a list of categories to break up the case into manageable lots. This can be simply a list of issues in the case. The embodiment given herein uses the example of banks, consulting contracts, governments contracts, taxes, and foreign subsidiaries. Again, these issues can be added or removed as the case progresses.

Figures 1B, 2:
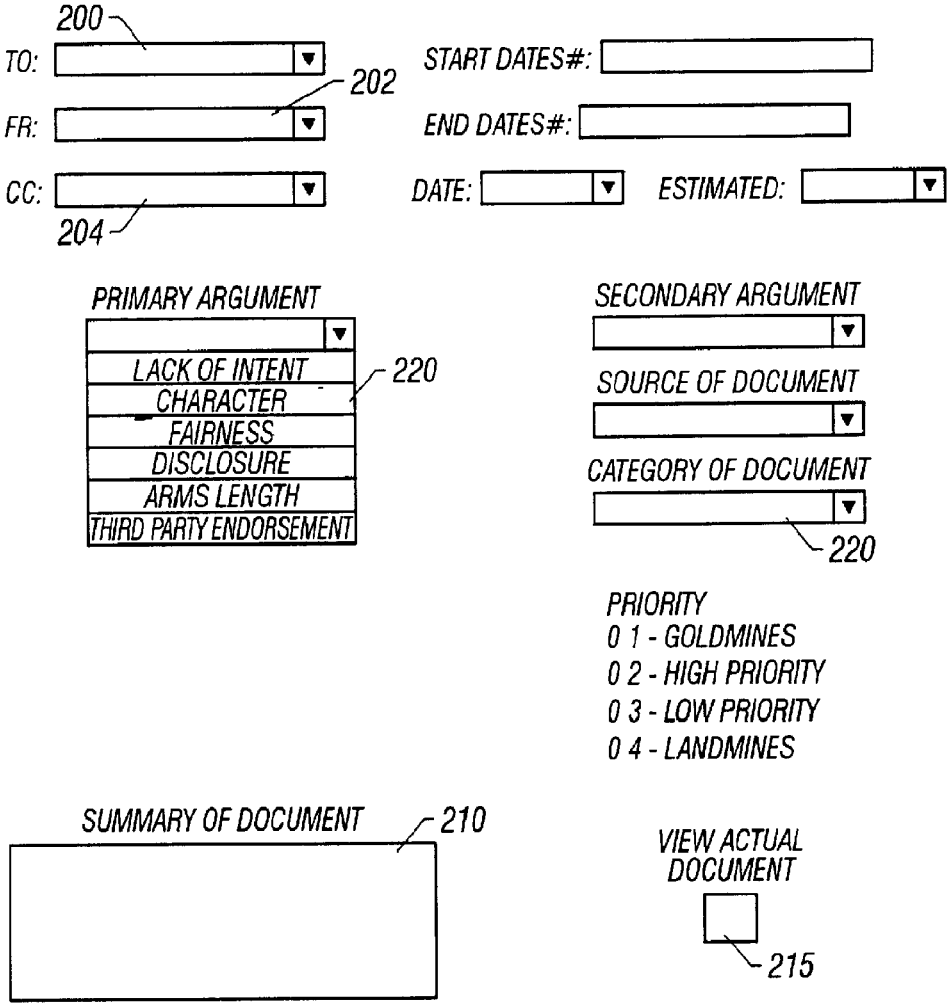

FIG. 1B shows the remainder of the specification information.

Field D is a list of sources of documents. Each time a document is added into the database, its source needs to be added.

Field E is a list of legal arguments that are anticipated. New elements of the legal case can be added as the case progresses.

Many of the fields in FIGS. 1A and 1B can be manually entered, or can be automatically generated by the entry of the documents into the database as described herein.

The specifications of the case are entered in the FIG. 3 flowchart at step 300. This loads the parameters that will be used to form the data entry interface shown in FIG. 2.

At step 302, the documents are scanned and optically character recognized ("OCR"). This operation preferably uses elements of the Adobe suite: Adobe Acrobat for the scanning, and Adobe Capture for the OCR. The scanned documents are scanned into the portable document format ("PDF"), which allows much greater flexibility in later manipulating these documents.

Step 304 illustrates automatically linking each scanned document to a new database record. That database record, at that time, has no information associated with it. The OCR information can be investigated to determine some of the by scanning for the keywords: To, From, cc, re. These fields can be used to automatically generate the respective fields.

Step 306 indicates the production of the FIG. 2 screen. The list boxes shown in FIG. 2 are automatically created based on the specifications of the case.

This can be done in Visual Basic by scrolling through each list of specifications, and adding each item to the list box. This might take the form:

```
For N=1 to Lastvalue
Category_Listbox.additem=Category_items(N)
Next N,
```

where Lastvalue is the number of category items, Category_Listbox is the name of the list box 220 for the categories, and Category_items(N) is the array of all items in the specification.

Other list boxes can be formed in an analogous way.

For example the list box 200 for "To:" is created from field B—all people who send, receive or copy documents. Similar operations create the list boxes 202 and 204 for FROM and CC. Similarly, the arguments, document source, category list boxes are automatically created.

Of course, other list boxes are possible. For example, a simple list box for document persons could be used to allow pulling all documents with to, from and cc.

The information about these fields is hence entered.

At step 308, the system automatically produces the pushbuttons, again based on the specifications of the case. These pushbuttons will be described later.

Step 310 illustrates entry of document information, corresponding to the scanned document, into the database.

The user enters the list box information by selecting items from the list boxes. This automatically enters that name in the fields relating thereto, without requiring the user to type this every time. These items can include author of the document, the recipient of the document or those carbon copied on the document, primary and secondary arguments, document category and document source.

Note that the user does not need any special training to select this information from the list boxes. Each of the list boxes has been automatically loaded with the different values based on the case specifications.

Other specifications can be manually entered.

The document can be prioritized as favorable (goldmines), unfavorable (landmines), high priority and low priority.

A summary 210 of each document can also be entered as part of the manual field entry in step 606. This summary is stored along with the document, and the words of this summary can be full text searched from the field 210 in FIG. 2.

Identifying numbers, such as "Bates" numbers, can also be added. At all times, the user can view the actual PDF document by actuating button 215, thereby calling Adobe Acrobat to read the associated PDF file.

Normally the user selects from the list box, although it is also possible for the user to type a name into the list box, in which case that name is added. The user has the additional option of modifying the initial start up screen specifications to add or delete entries on the list boxes and push buttons.

Figures 1B, 2:
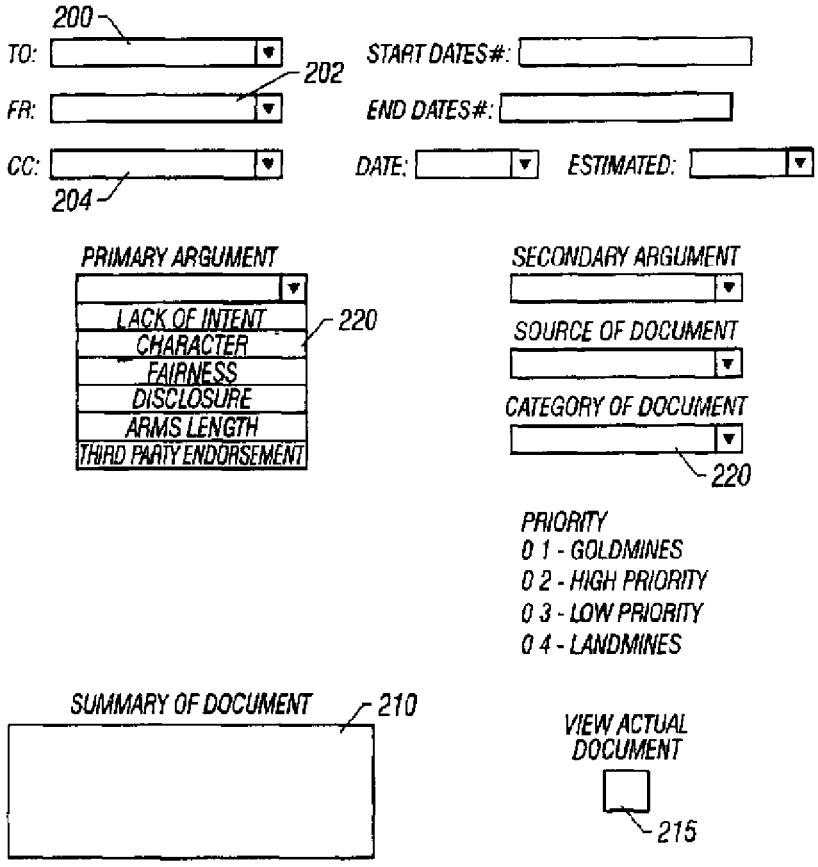

The FIG. 1 information needs to be entered only once. It can be updated each time the total set of information about the case changes. The FIG. 2 list boxes are automatically created from the FIG. 1 information, and comes up, however, each time the user wants to obtain any information.

Once the data has been entered, all evidence aligned to that data can be searched, as illustrated at step 312. This is preferably done by pressing the on-screen push button.

Those results are used to create a set of coded pushbuttons as shown in FIG. 4A. Each push button is associated with a single action. This can be done very simply in Visual Basic by creating one button for each search result, and changing each one button's text attribute to the attribute of the result. That one button's click event in Visual Basic is then associated with all the records that are associated with that one result.

The user can obtain, e.g., view and print, specific segments of information by simply selecting "pushing" any of the automatically-created coded push buttons.

FIG. 4A shows one screen of push buttons relating to the witnesses in the case. The screen includes buttons formed from the potential witnesses as entered in FIG. 1, field A, including the prosecution witnesses and the defense witnesses. Each of the witness names is used to form the text attribute of a command button, whose click event takes an action related to the witness name.

Specifically, when the user presses a specific button associated with a specific witness, a summary of all documents which the witness authored, received, was carbon copied on, or was mentioned in the summary is presented to the user in specified order, e.g., chronologically.

Hence, by selecting one button 400 from the screen shown in FIG. 4A, here "York", the user gets all the record information associated with that one witness. More generally, FIG. 4A can be formed for any keyword, e.g., any person, category or argument.

Figure 4C:
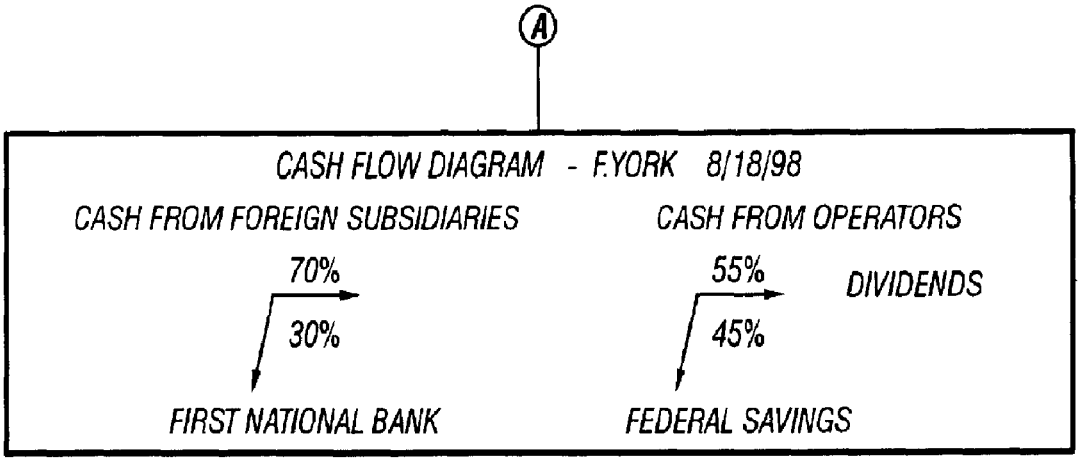

The information obtained by selecting the witness "York" is shown in FIG. 4B, including the Bates number or other identifying number of the document, date, Author, summary. Further, each record includes a button 350 to allow fetching the digital image of the actual document as entered during the document entry phase. This fetch operation preferably uses Adobe Exchange to fetch the PDF file. The user merely pushes that button to fetch and view or print the document of interest. FIG. 4C depicts the scanned version of the document that is obtained by selecting the view document button.

That document can be opened in a new window, for example, hence allowing the user to browse many different documents to find the best one.

Other fields are similarly used to automatically create their own screen of similar push buttons which allow simple selection of the information.

Figure 5:
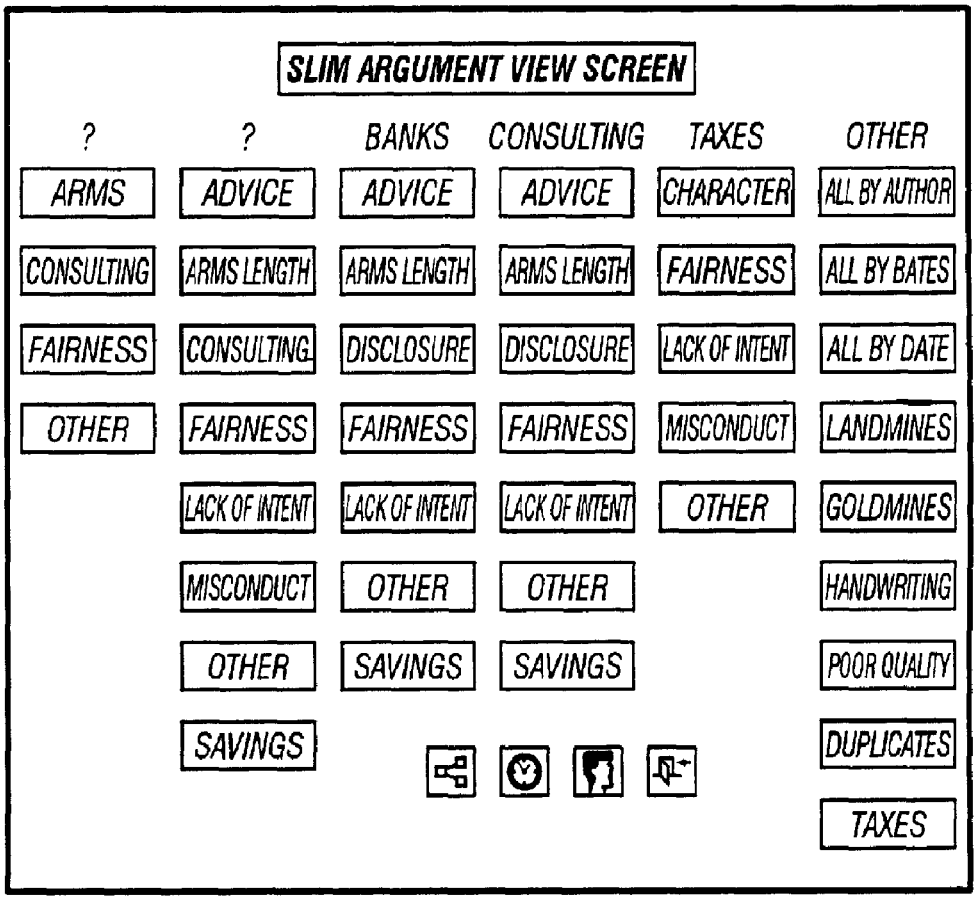
FIGS. 5 and 6 show specific push buttons produced from arguments of the case.

FIG. 5 illustrates the screen of push buttons created for the arguments of the case. Here each argument in the argument list box 220 in FIG. 2, created from the argument specifications field E in FIG. 1 is created into a box. FIG. 5 shows these being sorted by category: Banks, Consulting Contracts, etc. Once again, specific names on the buttons refer to a specific legal argument for a specific category. So if the user selects "fairness" as the Primary Argument, and Consulting Contract as the category, a summary of all documents sorted in chronological order that pertain to fairness of the consulting contracts will be presented.

Figure 6:
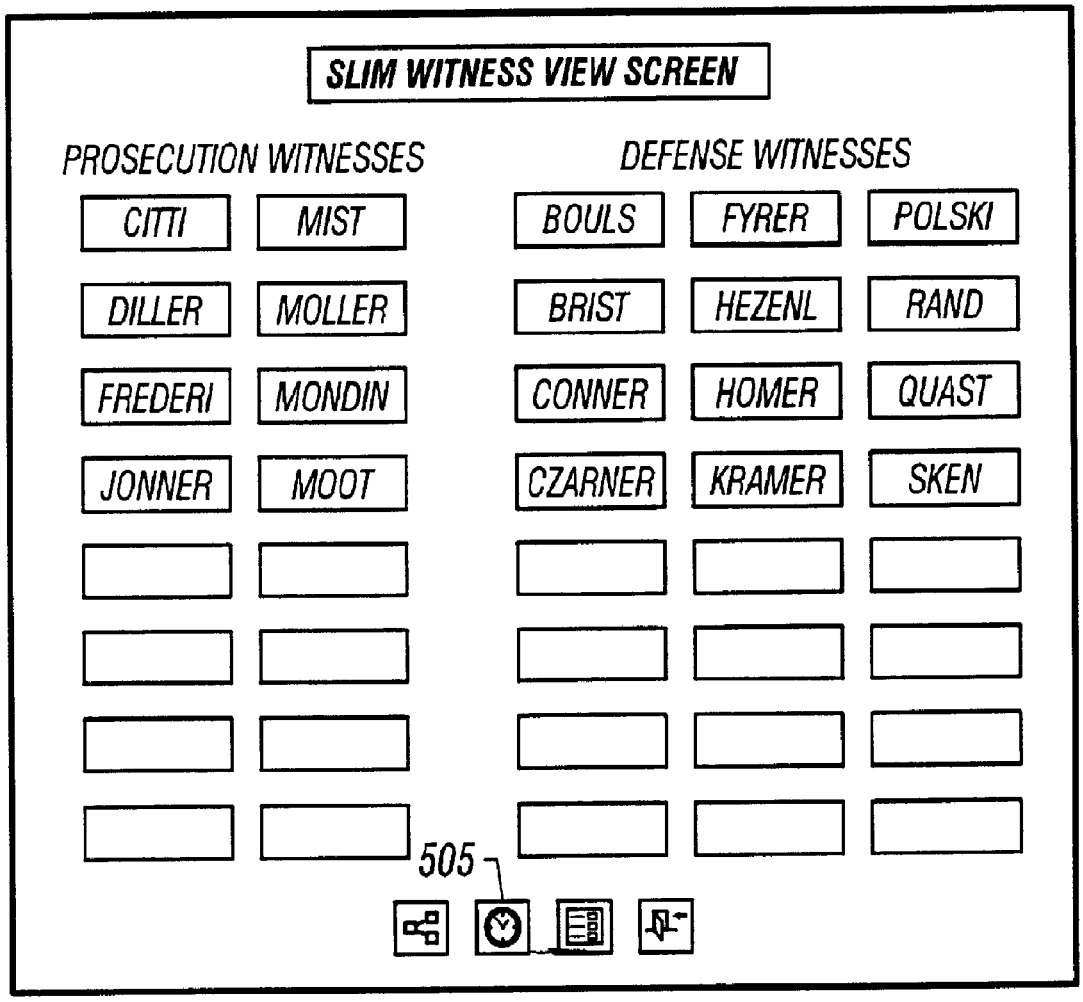

FIG. 6 similarly shows the witness push button screen, sorted into prosecution/defense, as in the specifications as entered.

When a button is pressed in FIGS. 5 or 6, a list like that in FIG. 3B is presented. The user can simply press any button 350 associated with each summary to view and print the actual document.

Figure 7:
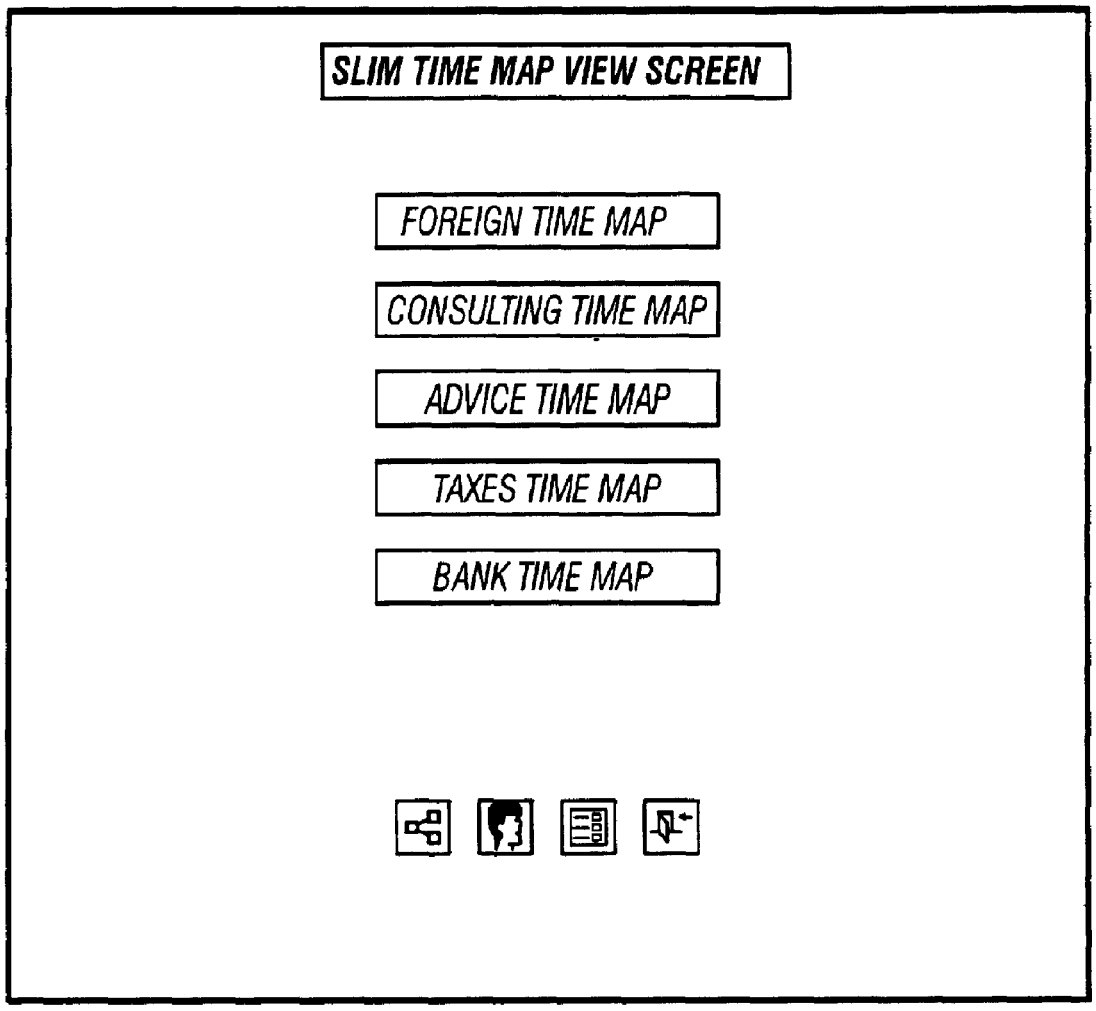
FIG. 7 shows an interface screen.
Figure 8:
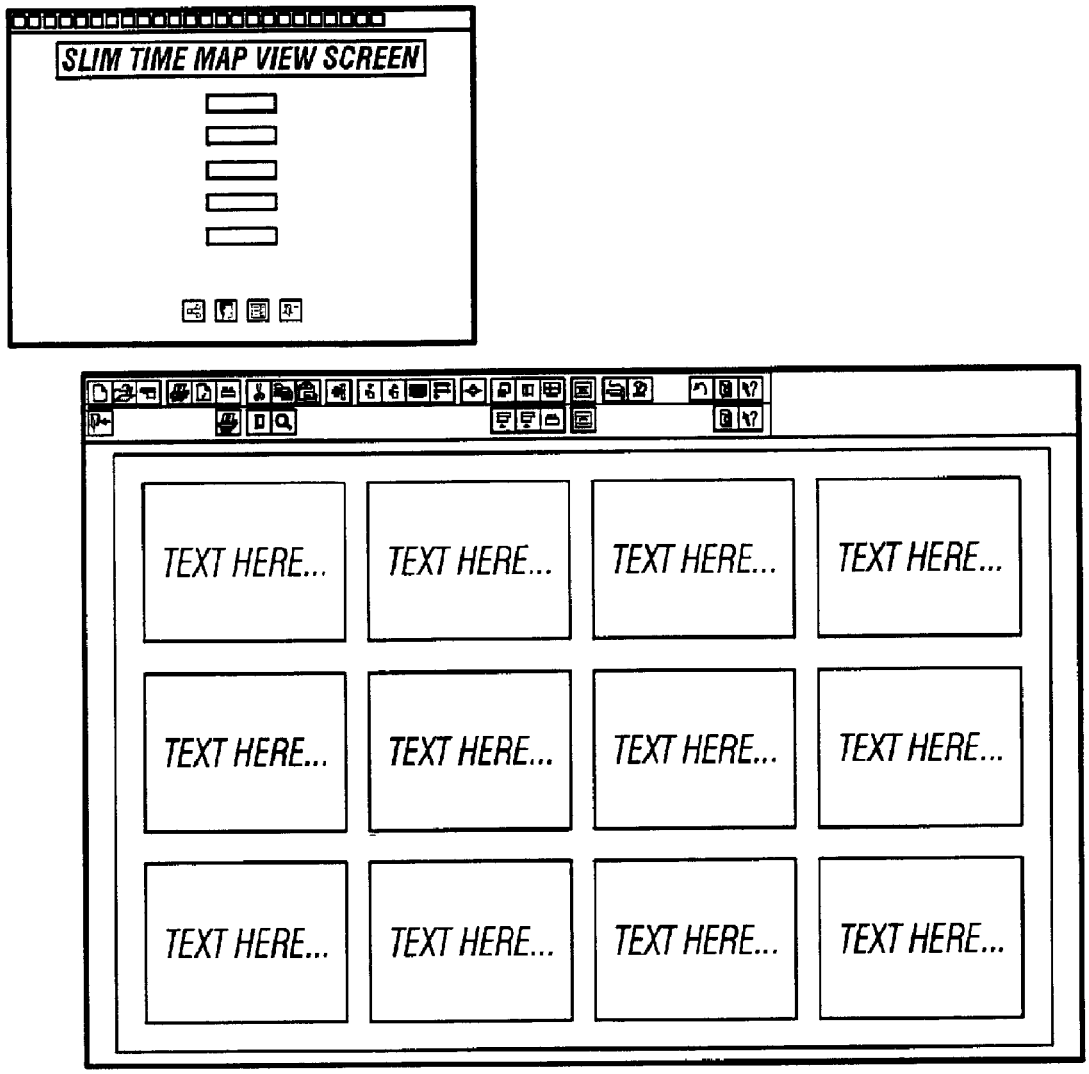
FIGS. 8 and 9 show time maps which are produced from the automatically created buttons.

Another option of this system is the time map view screen, obtained by pressing the time icon 505, shown in FIGS. 5 and 6. This creates a time map view screen for the selected screen. For example, the time map view screen for FIG. 5 is shown in FIG. 7. Actuating any of those automatically-created buttons brings up a time map shown in FIG. 8, where each summary of document is arranged in chronological order to determine time lines of those documents.

Figure 9:
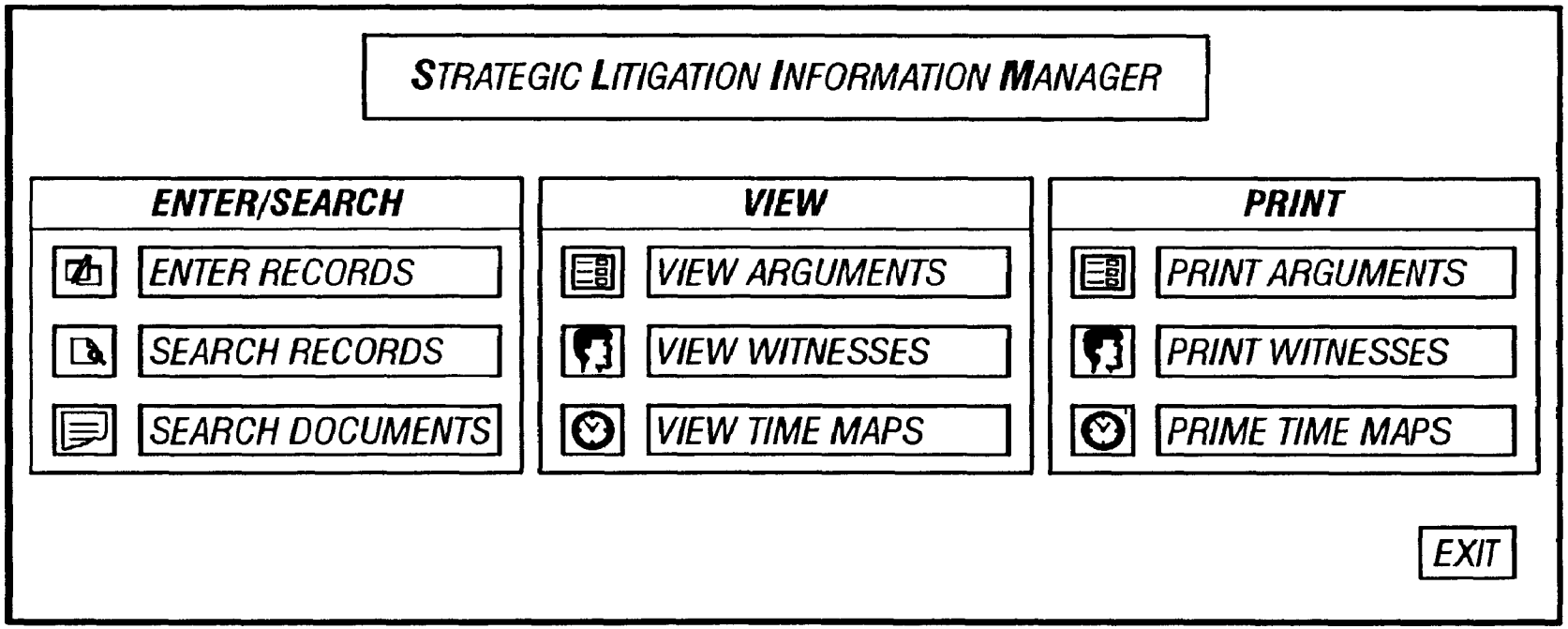

Any of these operations can also be selected from the overall manager screen shown in FIG. 9.

This preferred system described above is for an embodiment used in litigation support. However this system can be used for essentially all databases in the legal, medical, research and corporate areas. Key points of simplicity of this allow easy use.

Preferably all choices and selections to find information within the database are made by list boxes which list all possible selections; of which one or more can be selected: and/or by push buttons. As described in detail above, each push button is associated with one particular item, and its selection brings up that further information.

Another example is the user creating witness folders for direct or cross-examination which show a summary of the evidence for each witness in chronological order. The evidence could include memos the witness authored or received or was copied on, correspondence that mentioned the witness in the body of the report, summary description of the document where the user has indicated the name of the witness, the witness deposition, or other depositions where the name of the witness was mentioned.

Again, with the press of a button, the user can createchronological time maps of the evidence in the case as a whole or for a specific category or witness.

Allows for the isolation of key exculpatory evidence (goldmines) or inculpatory evidence (landmines). The user can quickly see legal argument reports showing all the evidence aligned to a specific issue or argument. A faithful replication of any document that has been identified from various database sorts or full-text searches can be viewed or printed almost instantly.

The user can use the power of the Adobe suite to search for documents in a variety of ways including full-text search, sounds-like search, thesaurus search, etc.

This new concept provides all the basic features of the leading litigation support software applications, SUMMATION(™) and CONCORDANCE(™), but offers significant advantages not available with any current database technology. The present system can be easily customized with push-buttons for each individual case by first entering on a start-up screen specifications for the case witnesses, legal arguments, sources of documents, categories, authors and recipients of documents, etc.

Also, after entering data with the aid of automatic list boxes which are generated from the first step, evidence can be sorted, searched and browsed with push-button efficiency. The need for extensive training and technical support will virtually be eliminated.

This system which automatically converts case specifications to push buttons significantly expands the use of database or document management programs to those not skilled in the area of computer programming. With this concept, literally anyone can enter the initial specifications of the case and immediately get push button screens to allow for unprecedented ease of use, specifically in fetching selected information which can otherwise only be made available with complex queries and computer programming.

Many different type of computer programming techniques can be used to accomplish this new concept of automatically converting specifications into push buttons. In this case, Visual Basic programming techniques were successfully used to accomplish the objective. Other programming techniques, including C++, Pascal, Fortran, or assembler, could also be used.

Although only a few embodiments have been described in detail above, those of skill in the art recognize that many modifications are intended and predictable from the disclosed embodiments.

For example, many different fields could be used and contemplated beyond the ones described herein.

The push buttons as described could be any selectable area associated with a title indicating what will happen when the area is selected. The title can be inside the selectable area as on a push button, or near it, or associated with the area in any other way.

Another contemplated extension is that data is automatically imported from an on-line source, such as the Internet, or LEXIS (™). For example, cases can be searched using the LEXIS (™) capability, and automatically added to the database.

In addition, other plug-in programs besides those described herein are contemplated. For example, double clicking on a number within a document could launch a spreadsheet program, such as Excel, which then automatically imports the contents of the document for tracking costs, for example.

All such modifications are intended to be encompassed within the following claims.

What is claimed is:

1. A method, comprising:

defining, *by a computing device,* a project [including] *having at least one field for association with documents, wherein the project includes* a list of project specifications *comprising lists of data values associated with the at least one field*;

[automatically] forming, *by the computer device, at least one* data entry [screens] *screen* based on said [original] list of project specifications *in response to defining the*

*project*, [each] *wherein* said *at least one* data entry screen [including] *includes* choices for said data entry that are automatically formed from said *list of* project specifications; and

[automatically] forming, *by the computer device,* search queries based on said [original] list of project specifications *in response to defining the project,* including choices for search queries that are formed automatically based on said project specifications.

2. A method as in claim 1, wherein said project is a legal case.

3. A method as in claim 1 wherein said data entry screens include pull down lists including said choices, each pull down list including a list of possible alternatives for said data entry screen.

4. A method as in claim 1, further comprising fill in capabilities, which allow additional information to be typed into the list box.

5. A method as in claim 4, further comprising allowing a user to remove a name from the list.

6. A method as in claim 1 wherein said search queries comprise a plurality of pushbutton elements, [each] *individual ones* of which [is] *are* associated with a textual command, and [each] *individual ones* of which can be selected to execute a search query associated with said textual command.

7. A method as in claim 6, further comprising ordering search results based on a specified order.

8. A method as in claim 7 wherein said specified order is chronological order.

9. A method as in claim 1, further comprising selecting a search, and, [after] *in response to* selecting said search, [automatically] forming additional search queries based on a narrowed down list of search queries.

10. A method as in claim 1 wherein said defining comprises scanning a document, optically character recognizing said document, and [automatically] creating records for the optically character recognized document *in response to the optical character recognizing*.

11. A method as in claim 10, wherein said [automatically] creating records comprises [automatically] creating database entries for each said document *in response to the optical character recognizing*.

12. A method as in claim 11, further comprising enabling selecting a database entry, wherein said enabling comprises [automatically] executing a program which enables viewing said database entry *in response to the creating records*.

13. A method as in claim 1 wherein said defining comprises [automatically] creating said project specifications [by] *in response to an* automatic entry of documents.

14. A method as in claim 1 wherein said defining a project comprises entering documents about a project, and categorizing said documents.

15. A method as in claim 1 further comprising [automatically] forming a time map of specifications within the project *in response to receiving a choice at the at least one data entry screen*.

16. A method as in claim 1 wherein said project is a medical project.

17. A method as in claim 1, further comprising enabling certain aspects of said project to be flagged as key aspects.

18. An article comprising a *tangible* computer readable *storage* media and storing computer executable instructions to organize a specified project, said [in] instructions [causing the computer] *configured to cause a computer* to *perform operations comprising*:

[enter] *receiving* information about a project, *the project having at least one field for association with documents, the information comprising lists of values associated with the at least one field*;

[automatically] forming data entry screens *in response to receipt of the information, the data entry screens* based on said information about said project; and

[automatically] forming search queries *in response to receipt of the information, the search queries* based on said information about said project.

19. An article as in claim 18, wherein said [enter] *receiving further* comprises [entering] *receiving* documents automatically, and causing information about said documents to [automatically] form said [data entry screens] *information about the project in response to receipt of the information*.

20. An article as in claim 18, wherein said project is one of a legal case, a medical case, a corporate case, or a research case.

21. An article as in claim 18, wherein said search queries are one of a pull down list box, or a pushbutton box.

22. An article as in claim 21, further comprising an additional function which enables said search queries to be expanded by adding or removing an item from said pull down box or said pushbutton box.

23. A method, comprising:

entering information about a project *using a computing device*, *the project having at least one field for association with documents, the information* including at least specifications about said project *comprising lists of values associated with the at least one field*, at least part of said entering including automatic determination of said information *using the computing device*;

based on said information, determining categories of information, and [automatically] forming data entry parameters based on said categories *via the computing device, in response to the entering*, said data entry parameters including a list of possible data entry parameters; and

[automatically] forming search queries based on said information *via the computing device, in response to the entering*, said search queries including a list of possible search queries.

24. A method as in claim 23 wherein said list comprises one of a pull down list or a pushbutton box with text therein.

25. A method as in claim 24, wherein said project is one of a medical project, a legal project, a corporate project, or research project.

26. A method as in claim 23 wherein said entering comprises obtaining electronic versions of documents, [first entering contact information, next,] entering names of fields which are related to one another, [next] entering potential lists of choices for each field, and forming records from said fields and linking said fields to specified electronic versions of documents.

27. A method as in claim 26, wherein said entering further comprises, for [each] *individual ones* of a plurality of documents, entering database information for said document based on said choices.

28. A method as in claim 26, wherein said [automatically] forming search queries [form] *comprises forming* said search queries [based on said] *in response to entering the potential lists of* choices.

*29. An apparatus comprising:*

*a computing device;*

*a database configured to store at least one project having at least one field associated with documents, the project also having at least one project specification comprising*

*lists of values associated with the at least one field, and wherein the database is accessible with the computing device;*

*a display device in communication with the computing device;*

*the computing device configured to form data entry screens for display on the display device based on the at least one project specification stored in the database, in response to receipt of the projection specifications, wherein project information is associated with values stored in the at least one project specification, and the computer is configured to form search queries based on the at least one project specification, in response to receipt of the project specifications, wherein the search queries retrieve project information associated with values stored in the project specification.*

*30. The apparatus of claim 29, wherein the data entry screens include choices for data entry that are formed from the at least one project specification, in response to receipt of the project specifications, and the search queries include choices that are formed based on the at least one project specification, in response to receipt of the project specification.*

*31. The apparatus of claim 29, wherein the data entry screens include pull down list boxes including a list of possible alternatives for the data entry screens.*

*32. The apparatus of claim 31, wherein the computer is configured to allow additional information to be typed into the pull down list box.*

*33. The apparatus of claim 32, wherein the computer is configured to allow removal of a name from the list of values associated with the at least one field.*

*34. The apparatus of claim 29, wherein the search queries comprise a plurality of pushbutton elements associated with a textual command which can be selected to execute a search query associated with the textual command.*

*35. The apparatus of claim 29, wherein the computer is configured to form additional search queries based on a narrowed down list of search queries, in response to selection of one of the search queries, wherein the additional search is performed subsequent to a first search query.*

*36. The apparatus of claim 29, wherein the computer is configured to scan a document, optically character recognize the document, and create records for the optically character recognized document in response to optical character recognition.*

*37. The apparatus of claim 36, wherein the computer is configured to populate the at least one field for individual ones of the documents in response to optical character recognition.*

*38. The apparatus of claim 36, wherein the computer is configured to create the project specifications by automatic entry of documents in response to optical character recognition.*

*39. The apparatus of claim 29, wherein the computer is configured to form a time map of specifications within a project in response to receipt of data entry.*

*40. The apparatus of claim 29, wherein the computer is configured to enable certain aspects of a project to be flagged as key aspects.*

*41. An apparatus comprising:*

*means for computing;*

*means for storing a project comprising at least one field associated with documents, the project further comprising a plurality of project information and one or more project specifications comprising lists of values associated with a plurality of fields, wherein values associated with the fields differentiate individual ones of the project information, and wherein the means for storing is configured to be accessed by the computing means; and*

*means for causing the computing means to form data entry screens based on the one or more project specifications, in response to receipt of project information, wherein project information is associated with values stored in the project specification, and means for causing the computing means to form search queries based on the one or more project specifications in response to receipt of project information.*

*42. The apparatus of claim 41, comprising means for causing the computing means to form additional search queries based on a narrowed down list of search queries, in response to selection of a search query, wherein the additional search is performed subsequent to a first search query.*

*43. The apparatus of claim 41, further comprising means for causing the computing means to create the project specifications in response to automatic entry of documents.*

*44. The apparatus of claim 41, further comprising means for enabling certain aspects of a project to be flagged as key aspects.*

* * * * *

UNITED STATES PATENT AND TRADEMARK OFFICE

CERTIFICATE OF CORRECTION

PATENT NO. : RE43,391 E
APPLICATION NO. : 11/965372
DATED : May 15, 2012
INVENTOR(S) : Costin et al.

It is certified that error appears in the above-identified patent and that said Letters Patent is hereby corrected as shown below:

On the Title Page, in Field (56), under "OTHER PUBLICATIONS", in Column 2, Line 1, delete "Mcmanus ,Publisher:" and insert -- Mcmanus, Publisher: --, therefor.

In Fig. 1A, Sheet 1 of 8, Line 18, delete "CATAGORIES" and insert -- CATEGORIES --, therefor. (See attached)

In Fig. 1B, Sheet 2 of 8, delete "THIRD PARTY ENDORSMENT" and insert -- THIRD PARTY ENDORSEMENT --, therefor. (See attached)

In Column 1, Line 14, delete "Ser." and insert -- Appl. Ser. --, therefor.

In Column 1, Line 62, delete "fields" and insert -- fields. --, therefor.

In Column 1, Line 67, delete "etc" and insert -- etc. --, therefor.

In Column 2, Line 1, delete "layout" and insert -- layout. --, therefor.

In Column 2, Line 2, delete "data" and insert -- data. --, therefor.

In Column 2, Line 4, delete "tables" and insert -- tables. --, therefor.

In Column 2, Lines 5-6, delete "information" and insert -- information. --, therefor.

In Column 2, Line 8, delete "data" and insert -- data. --, therefor.

In Column 2, Line 11, delete "features" and insert -- features. --, therefor.

In Column 2, Line 14, delete "steps!" and insert -- steps. --, therefor.

Signed and Sealed this
Twenty-seventh Day of November, 2012

David J. Kappos

David J. Kappos
*Director of the United States Patent and Trademark Office*

In Column 3, Line 57, delete “push-button controls.” and insert -- push button controls. --, therefor.

In Column 4, Line 31, delete “DESCRIPTION” and insert -- DETAILED DESCRIPTION --, therefor.

In Column 5, Line 6, delete “governments” and insert -- government’s --, therefor.

In Column 6, Line 33, delete “pushbuttons” and insert -- push buttons --, therefor.

In Column 7, Line 45, delete “selected:” and insert -- selected; --, therefor.

In Column 7, Lines 58-59, delete “createchronological” and insert -- create chronological --, therefor.

In Column 8, Line 10, delete “case witness,” and insert -- case witnesses, --, therefor.

A. LIST POTENTIAL WITNESSES

| PROSECUTION | DEFENSE |
|---|---|
| JOHN DOE | JIM JONES |
| AL JACKSON | DICK KINDER |
| GLORIA TIMS | DEE CLARKS |
| SUE ALKS | JOE MANNS |
| FRED YORK | JENNY BICS |

B. LIST PEOPLE WHO SEND, RECEIVE OR ARE COPIED ON MEMOS AND CORRESPONDENCE

| | | |
|---|---|---|
| AL KILKA | FRED YORK | JENNY BICS |
| JOE CURL | JIM JONES | TOM ULNER |
| SALLY DOPER | JUDY KALMER | BING STUBY |
| JUDY FIELDS | DICK KINDER | CAROL SLIP |
| JOHN DOE | DEE CLARKS | KIM CARASONS |
| AL JACKSON | JIM GRANDER | JOHN JENSEN |
| TIM YANS | DEB DUCKER | HEATHER BATIA |
| AL YU | | |

C. LIST CATEGORIES

BANKS

CONSULTING CONTRACTS

GOVERNMENT CONTRACTS

TAXES

FOREIGN SUBSIDIARIES

FIG. 1A

D. LIST SOURCES OF DOCUMENTS

DEPOSITION
BANKS
NEWS
COMPANY A
MOTIONS
COMPANY B
CASE LAW
COMPANY C

E. LIST LEGAL ARGUMENTS ANTICIPATED

LACK OF INTENT
CHARACTER
FAIRNESS
DISCLOSURE
ARMS LENGTH
THIRD PARTY ENDORSEMENT